United States Patent [19]

Ware et al.

[11] Patent Number: 4,843,185

[45] Date of Patent: Jun. 27, 1989

[54] METHOD FOR ENHANCING THE POLYMERIZATION ACTIVITY OF CRUDE CYCLOOLEFIN MONOMERS FOR BULK POLYMERIZATION

[75] Inventors: James T. Ware, Doylestown; Robert J. Minchak, Parma Heights, both of Ohio

[73] Assignee: The B. F. Goodrich Company, Akron, Ohio

[21] Appl. No.: 179,253

[22] Filed: Apr. 8, 1988

[51] Int. Cl.$^4$ ................................................ C07C 7/00
[52] U.S. Cl. .................................... 585/803; 585/360; 585/518; 585/899; 526/75
[58] Field of Search ............... 585/360, 518, 803, 899; 526/75

[56] References Cited

U.S. PATENT DOCUMENTS

| | | |
|---|---|---|
| 3,701,812 | 10/1972 | Gebhart, Jr. et al. . |
| 3,778,420 | 12/1973 | Brown et al. . |
| 3,781,257 | 12/1973 | Pampus et al. . |
| 3,790,545 | 2/1974 | Minchak . |
| 3,793,381 | 2/1974 | Kohler et al. ........................ 585/803 |
| 3,853,830 | 12/1974 | Minchak . |
| 3,855,326 | 12/1974 | Joy et al. ............................ 585/803 |
| 4,002,815 | 1/1977 | Minchak . |
| 4,136,247 | 1/1979 | Tenney et al. . |
| 4,136,248 | 1/1979 | Tenney . |
| 4,136,249 | 1/1979 | Tenney et al. . |
| 4,168,282 | 9/1979 | Schneider . |
| 4,178,424 | 12/1979 | Tenney et al. . |
| 4,320,239 | 3/1982 | Schneider . |
| 4,703,098 | 10/1987 | Matlack . |
| 4,748,216 | 5/1988 | Tom . |
| 4,751,337 | 6/1988 | Espy et al. . |

*Primary Examiner*—Curtis R. Davis
*Attorney, Agent, or Firm*—Robbins & Laramie

[57] ABSTRACT

A process for enhancing the polymerization activity of mixtures of one or more cycloolefin monomers is provided by treatment with heat. This process can be easily incorporated into ring-opening, bulk polymerization methods and methods which form high molecular weight monomers. Enhancing the polymerization activity of crude mixtures of cycloolefin monomers by this process permits polymers having higher glass transition temperatures and higher heat distortion temperatures to be produced with greater economy.

16 Claims, No Drawings

METHOD FOR ENHANCING THE POLYMERIZATION ACTIVITY OF CRUDE CYCLOOLEFIN MONOMERS FOR BULK POLYMERIZATION

RELATED APPLICATIONS

This application is related to copending application Ser. No. 122,849 filed Nov. 19, 1987.

FIELD OF THE INVENTION

This invention is directed to improving the quality of crude cycloolefin monomers which contain a norbornene group. More particularly, this invention is directed to a method for enhancing the polymerization activity of crude cycloolefin monomers for polymerization in bulk, such as by reaction injection molding (RIM) techniques, to provide copolymers with high heat stability.

BACKGROUND OF THE INVENTION

Cycloolefin monomers (cycloolefins) which contain a norbornene group are known to polymerize by ring-opening polymerization and addition polymerization. Polymers obtained by ring-opening polymerization of cycloolefins that contain a norbornene group are well known. For example, U.S. Pat. Nos. 4,136,249; 4,178,424; 4,136,247 and 4,136,248, assigned to the same assignee of the present invention, describe such polymers, and each is incorporated herein by reference for the description of polymers therein.

Ring-opening polymerization of cycloolefins yields unsaturated linear polymers which are of particular interest in that they are known to be reactive (sulfur-vulcanizable) and they are known to exhibit attractive property profiles with good heat distortion temperatures for many polymer applications, such as, for example, as automotive parts, particularly body panels, bumpers, facia, etc. Many of these polymer properties, such as heat distortion temperature, are dependent on a high degree of conversion of the cycloolefin monomer into polymer. This is particularly true in bulk polymerization processes where any unreacted monomer will remain dispersed in the finished article, providing an undesired plasticizing effect and/or this unreacted monomer may leach from the molded part, rending the finished article less useful. It is known a substantially pure feedstock of cycloolefin monomers will help provide a high degree of conversion in bulk polymerization processes, and may often be necessary to provide useful finished articles. A cycloolefin monomer feedstock of over 99% purity is often desired in RIM techniques, which is a common example of a bulk polymerization process.

Dicyclopentadiene is a common cycloolefin monomer used to prepare ring-opening polymerized polymers. Recent U.S. Patents directed to dicyclopentadiene polymers include U.S. Pat. Nos. 3,778,420; 3,781,257; 3,790,545; 3,853,830 and 4,002,815. Dicyclopentadiene monomers are by-products in ethylene production and are commercially available in different grades of purity. The commercial crude grades of 97% to 98% dicyclopentadiene do not yield the rapid reactions nor high conversion desired for ring-opening polymerization. The more costly 99% pure dicyclopentadiene shows the necessary quality for both high activity and high conversion. It is desirable to develop a simple means to enhance the polymerization activity of the less pure dicyclopentadiene grades to provide the desired activity and conversion.

Purification of other cycloolefin monomers for use in ring-opening bulk polymerizations is also desired. For example, norbornene (bicyclo(2.2.1)hept-2-ene), substituted norbornenes, tetracyclododecene, substituted tetracyclodocenes, and higher homologs of these with cyclopentadiene, are known to be produced by the Diels-Alder reaction of cyclopentadiene and selected olefins. Often a mixture of products is obtained from these reactions, requiring purification. A less costly purification process would be a great advantage in utilizing the cycloolefin monomers synthesized from dicyclopentadiene.

In copending application, Ser. No. 122,849, filed Nov. 19, 1987, heat treatment of a polymerization grade cycloolefin feedstock was found to yield a product containing cycloolefins with increased molecular weight. The heat treatment did not affect the reaction rate or the degree of conversion of the monomers. The monomers were still of polymerization grade after heat treatment.

It has now been discovered that the heat-soaking porcedure (or heat treatment) of commercial crude grade 97–98% pure dicyclopentadiene enhances its polymerization activity by reducing the quantity of polymerization retarding impurities. This treated crude dicyclopentadiene provides the rapid polymerization rates and high monomer conversion desired from the high quality, commercial polymerization grade, 99% pure dicyclopentadiene.

SUMMARY OF THE INVENTION

This invention provides a method for enhancing the polymerization activity of crude grade mixtures of cycloolefin monomers to provide a feedstock suitable for bulk polymerization. This is accomplished by heating a crude mixture of one or more cycloolefin monomers containing polymerization retarding impurities wherein the cycloolefin monomers have at least one norbornene group. The cycloolefin monomers are preferably bicycloolefins and tricycloolefins such as dicyclopentadiene.

This crude grade mixture of one or more cycloolefin monomers is heated to a temperature sufficiently high and for a period sufficiently long to dissociate a portion of the cycloolefin monomers, giving cyclopentadiene therein, and to react the cyclopentadiene product with polymerization retarding impurities in the crude mixture, such as linear olefinic impurities and oxygen containing impurities. The crude mixture of cycloolefin monomers is maintained substantially free of a complete polymerization catalyst/co-catalyst system during heating to prevent polymerization.

Another embodiment of this invention is a ring-opening bulk polymerization process wherein a crude mixture of one or more cycloolefin monomers, comprising at least 25% by weight dicyclopentadiene based on the weight of said crude mixture, is heated or heat-soaked to increase polymerization activity and is then bulk polymerized to obtain ring-opened polymerized polymers having high glass transition temperature values.

Also provided by this invention are methods for producing polymers from a crude mixture of one or more cycloolefin monomers by ring-opening bulk polymerization wherein the cycloolefin monomers are heated to provide both (1) an improvement in polymerization activity (or monomer quality) and (2) an increase in the molecular weight of the cycloolefin monomers.

DETAILED DESCRIPTION OF THE PREFERRED EMBODIMENTS

The invention herein is based on the discovery that crude mixtures of cycloolefin monomers such as dicyclopentadiene, which normally contain polymerization retarders such as linear olefins and diolefins and often oxygen containing products, can be improved in polymerization quality when heated to cause dissociation of the cycloolefin monomers giving cyclopentadiene. The dissociation of the cycloolefin monomers is advantageous to the polymerization quality of such a crude cycloolefin mixture in that cyclopentadiene reacts or renders harmless the polymerization retarders therein, such as the linear olefins and diolefins. It is preferred that dicyclopentadiene be present within the cycloolefin monomers utilized.

The cyclopentadiene may also react with the norbornene group of other cycloolefin monomers within the mixture, thereby forming cycloolefin monomers with increased molecular weight. The quantity of cyclopentadiene within the volume of cycloolefin monomers remains low because of their reactivity in forming Diels-Alder products with olefinics. This small quantity of cyclopentadiene does not affect the degree of conversion of the cycloolefin monomers in ring-opening polymerization procedures in that cyclopentadiene also participates in the bulk polymerization.

The one or more cycloolefin monomers which can be treated by the process described herein to provide enhanced polymerization activity are characterized by the presence of at least one norbornene group represented by Formula I below, which can be substituted or unsubstituted.

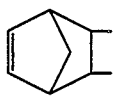

I

Pursuant to this definition, suitable cycloolefin monomers include substituted norbornenes and unsubstituted norbornene, dicyclopentadiene, dihydrodicyclopentadiene, cyclopentadiene trimers, cyclopentadiene tetramers, cyclopentadiene pentamers, tetracyclododecene, substituted tetracyclododecenes and hexacycloheptadecene. The more common cycloolefin monomers conform to Formulas II, III and IV below:

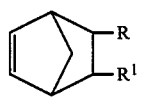

II

III

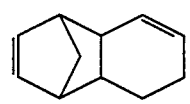

IV wherein R and $R^1$ are independently selected from hydrogen, halogen, $C_1$–$C_{12}$ alkyl groups, $C_2$–$C_{12}$ alkylene groups, $C_6$–$C_{12}$ cycloalkyl groups, $C_6$–$C_{12}$ cycloalkylene groups and $C_6$–$C_{12}$ aryl groups or R and $R^1$ together form saturated or unsaturated cyclic groups of from 4 to 12 carbon atoms with the two ring carbon atoms connected thereto, said ring carbon atoms forming part of and contributing to the 4 to 12 carbon atoms in the cyclic group. Examples of common cycloolefin monomers conforming to Formulas II and III include 2-norbornene,
5-methyl-2-norbornene,
5,6-dimethyl-2-norbornene,
5-ethyl-2-norbornene,
5-ethylidenyl-2-norbornene,
5-butyl-2-norbornene,
5-hexyl-2-norbornene,
5-octyl-2-norbornene,
5-dodecyl-2-norbornene,
5-isobutyl-2-norbornene,
5-octadecyl-2-norbornene,
5-isopropyl-2-norbornene,
5-phenyl-2-norbornene,
5-p-toluyl-2-norbornene,
5-α-naphthyl-2-norbornene,
5-cyclohexyl-2-norbornene,
5,5-dimethyl-2-norbornene,
dicyclopentadiene (or cyclopentadiene dimer),
dihydrodicyclopentadiene (or cyclopentene-cyclopentadiene co-dimer),
methyl-cyclopentadiene dimer,
ethyl-cyclopentadiene dimer,
tetracyclododecene
9-methyltetracyclo[6,2,1,1$^{3,6}$,0$^{2,7}$]dodecene-4, (or 9-methyltetracyclododecene-4 or methyltetracyclododecene)
9-ethyltetracyclo[6,2,1,1$^{3,6}$,0$^{2,7}$]dodecene-4, (or 9-ethyltetracyclodedecene-4 or ethyl-tetracyclododecene)
9-propyltetracyclo[6,2,1,1$^{3,6}$,0$^{2,7}$]dodecene-4,
9-hexyltetracyclo[6,2,1,1$^{3,6}$,0$^{2,7}$]dodecene-4,
9-decyltetracyclo[6,2,1,1$^{3,6}$,0$^{2,7}$]dodecene-4,
9,10-dimethyltetracyclo[6,2,1,1$^{3,6}$,0$^{2,7}$]dodecene-4,
9-methyl,10-ethyltetracyclo[6,2,1,1$^{3,6}$,0$^{2,7}$]dodecene-4,
9-cyclohexyltetracyclo[6,2,1,1$^{3,6}$,0$^{2,7}$]dodecene-4,
9-chlorotetracyclo[6,2,1,1$^{3,6}$,0$^{2,7}$]dodecene-4,
9-bromotetracyclo[6,2,1,1$^{3,6}$,0$^{2,7}$]dodecene-4,
cyclopentadiene trimer,
methyl-cyclopentadiene trimer,
ethyl-cyclopentadiene trimer,
dihydro-cyclopentadiene trimer, and the like.

The most common cycloolefin monomer is dicyclopentadiene. It is commercially available at various grades of purity. Dicyclopentadiene is also the preferred cycloolefin monomer because it cracks to cyclopentadiene at lower temperatures than the other cycloolefin monomers of formulas II and III. The crude cycloolefin monomer mixture generally contains at least 10% by weight, preferably at least 25% by weight, dicyclopentadiene, to provide cyclopentadiene dissociation products.

The most common crude grades of dicyclopentadiene contain various polymerization retarders such as linear olefins and diolefins from the synthesis of the cycloolefin monomers. Olefin functionality is evidenced by the reactivity of the impurities with the dicyclopentadiene reaction product. The process of this invention will readily improve the polymerizability of such mixtures by reacting the olefinic impurities therein with the cyclopentadiene dissociation product formed during cracking. The process of this invention is also capable of reducing the quantity of reactive polymerization retarders from other sources, such as from the degradation of the cycloolefin monomers or from contamination by unclean equipment or from intentional addition of such retarders. Oxygen containing compounds, such as oxides and epoxides, may also be present in crude mixtures of cycloolefin monomers and they are also polymerization retarders.

The identity and source of some polymerization retarders is difficult to determine by conventional techniques because of the small quantities present in the crude mixture. Gas chromatography in combination with mass spectroscopy may be helpful as an identification tool. In addition, mixtures of polymerization retarders may be expected, making their indentification and their source more difficult to determine. The type of polymerization retarders in the cycloolefin mixture will vary due to many factors, such as, for example, the cycloolefin monomers within the crude mixture, the starting materials used in synthesizing these cycloolfin monomers, the conditions which generated the impurities, etc.

The process of this invention will provide polymerization grade cycloolefin monomer products from crude grade cycloolefin monomers having higher levels of polymerization retarders than commercial crude grade 97–98% dicyclopentadiene. The process of this invention will handle quantities of polymerization retarders of over 5% by weight of the total cycloolefin monomers. The process of this invention is ineffective in reducing the quantity of saturated impurities. However, these saturated impurities will not hinder the effectiveness of the process of the invention in reducing the linear olefinic impurities and other polymerization retarders present in the crude mixture.

The level of polymerization retarders which can be handled is dependent on the quantity of dicyclopentadiene within the cycloolefin monomers treated. There must be sufficient dicyclopentadiene to crack to cyclopentadiene and react with olefinic impurities and tie up, eliminate or reduce the retarding effect of oxygen containing impurities so that polymerization grade monomer results. The identification of these polymerization retardants is complicated by (1) the small quantities present, (2) the large variety of species present, such as the oxygen containing compounds, and (3) the presence of inert impurities. Therefore, the most convenient method for determining feedstock quality and utility for use in the process of the invention is to sample the feedstock, apply the process of this invention to the sample and analyze the polymerization of the monomer feedstock sample.

As indicated above, the polymerization retarders reduce the degree of monomer conversion to polymer product. These polymerization retarders are generally present in crude cycloolefin mixtures in quantities less than 0.25 weight percent and as high as 1 to 10 weight percent. The quantity of these polymerization retarders generally reduces the degree of conversion of monomer to polymer by at least 1%. The polymerization retarders within the crude mixtures of cycloolefin monomers are preferably reduced or rendered inert to a level sufficiently low to permit at least about 90% conversion of the cycloolefin monomers to polymer and to provide an increase in monomer conversion of at least 1% and up to 10% or more as determined by the difference in weight of a polymerized sample before and after thermal gravimetric analysis on a DuPont 1090 thermal analyzer on heating a sample up to about 400° C. Obtaining a degree of conversion higher than 97% is more desirable and approaching 100% conversion of cycloolefin monomer is most preferred. The quantity of dicyclopentadiene may decrease after heat treatment where a portion dissociates to react with any olefinic impurities.

After enhancing their polymerization activity by the process of this invention, the cycloolefin monomers are formulated into a feedstock. The bulk polymerization feedstock may contain constituents other than the cycloolefin monomers. Other components of the polymerization feedstock may include the polymerization catalyst components and common additives. The components of the complete catalyst/co-catalyst system are generally separated into two or more streams of the heat-treated mixture of cycloolefin monomers. All components of the catalyst cannot be present within the treated mixture of cycloolefin monomers in that polymerization will commence. Either the catalyst or co-catalyst component may be present within a heat-treated mixture before use, but not both. Where desired, two separate heat-treated mixtures may be provided, one with catalyst and the other co-catalyst. Both heat-treated mixtures are then combined to form the complete catalyst/co-catalyst system and initiate polymerization.

For certain bulk polymerization processes, it may be most convenient for the catalyst or co-catalyst to be present during heat treatment of the crude mixtures by the process of this invention. It is recognized however, that these compounds may be added to the crude mixtures after heat treatment and still provide bulk polymerization.

Examples of bulk polymerization catalysts include, the organoammonium molybdates and tungstates represented by the formulas below:

$$[R^2_4N]_{(2y-6x)}M_xO_y \qquad \qquad V$$

and $$[R^3_3NH]_{2y-6x}M_xO_y \qquad \qquad VI$$

wherein O represents oxygen; M represents either molybdenum or tungsten; x and y represent the number of tungsten/molybdenum and oxygen atoms in the molecule based on a valance of +6 for molybdenum, +6 for tungsten and −2 for oxygen; and the $R^2$ and $R^3$ substituents can be the same or different and are selected from hydrogen, alkyl and alkylene groups each containing from 1 to 20 carbon atoms and cycloaliphatic groups each containing from 5 to 16 carbon atoms. All of the $R^2$ and $R^3$ substituents cannot be hydrogens nor be small in number of carbon atoms in that such a condition will render the molecule essentially insoluble in hydrocarbons and most organic solvents.

A more detailed description of these organoammonium molybdates and tungstates appears in U.S. Pat. No. 4,426,502, assigned to the same assignee as the present invention which is incorporated herein by reference. Specific examples of suitable organoammonium molybdates and tungstates include tridodecylammonium molybdates and tungstates, methyl tricaprylammonium molybdates and tungstates, tri(tridecyl- )ammonium molybdates and tungstates and trioctylammonium molybdates and tungstates.

The presence of these bulk polymerization catalysts or co-catalysts within the crude mixture of cycloolefin monomers does not inhibit the objectives of the present invention in providing purified cycloolefin monomers for polymerization in bulk. The quantity of catalyst or co-catalyst present is generally dictated by the needs of the subsequent bulk polymerization reaction and the resulting products desired.

Examples of co-catalysts used in bulk polymerizations are aryloxyalkylaluminum halides and alkoxyalkylaluminum halides of the formula $(R^4O)_a R^5{}_bAlX_c$, where $R^4$ is an alkyl or phenyl group containing about 1 to 18 carbon atoms, preferably 2 to 4; $R^5$ is an alkyl group containing 1 to 18 carbon atoms, preferably 2 to 4; X is a halogen selected from chlorine, iodine, bromine and fluorine, preferably chlorine and iodine; "a" is the number of equivalents of the alkoxy or aryloxy moiety and can vary from about ½ to about 2, preferably from about 1 to about 1½; "b" is the number of equivalents of the alkyl group and can vary from a minimum of about ¾ to a maximum of about 2, preferably from about ½ to about 1; and "c" is the number of equivalents of halogen and can vary from a minimum of about ½ to a maximum of about 2, preferably from about ¾ to about 1 ⅜. The sum of a, b, and c must equal 3.0.

For bulk polymerization, the organoammonium molybdate or tungstate or a mixture thereof, is generally employed at a level of about 0.01 to 50 milimoles molybdenum or tungsten per mole of total cycloolefin monomer, preferably 0.1 to 10 millimoles. The molar ratio of alkylaluminum halide to the organoammonium molydate and/or tungstate is not critical and can be in the range of about 200:1 and above to about 1:10 and is preferably from 10:1 to 2:1 of aluminum to molydenum or tungsten.

Conventional additives may also be introduced to the crude grade of cycloolefin monomers without inhibiting the objectives of the present invention in providing high quality cycloolefin monomers for bulk polymerization. These conventional additives include antioxidants such as Ethyl 330, a hindered phenol antioxidant; impact modifiers such as the Kraton series provided by Shell Oil Company, which are generally styrene-butadiene-styrene block copolymers; flame retardants such as antimony oxide and organohalides (decabromodiphenylether); fillers such as glass or carbon fibers; pigments such as titanium dioxide; etc. The amount of each additive present in said volume is preferably that which provides the desired additive effect to the finished polymerized polymer.

Upon obtaining a crude mixture of one or more cycloolefin monomers with olefinic impurities, this crude mixture of cycloolefin monomers is heated to a temperature sufficiently high to dissociate a portion of these monomers and react the cyclopentadiene product to reduce or render inert the polymerization retarders therein, such as linear olefinic impurities. The dissociation of the dicyclopentadiene monomer yields cyclopentadiene units which will react with linear olefinic impurities. The cyclopentadiene will also react with other components of the crude mixture of cycloolefin monomers, including the norbornene structures of the remaining cycloolefin monomers, thus increasing their molecular weight. This may also include monocyclic olefins or the conventional additives, i.e. flame retardants, impact modifiers, etc. added to the crude mixture of cycloolefin monomers.

Temperatures in the range of 60° to 250° C. are preferred for use with a crude mixture of dicyclopentadiene monomers. Most preferably, the temperature is maintained within the range of about 100° C. to 175° C. for dicyclopentadiene monomers of about 96–98% purity.

The volume of cycloolefin monomers is maintained at an elevated temperature for at least about 0.25 hours and preferably from about 1 to 6 hours, most preferably about 5 hours, within a pressure vessel. The extent of dissociation and reaction varies with the time and temperature utilized. The higher temperatures provide rapid dissociation, permitting shorter heating periods.

The extent of dissociation can be controlled by the temperature utilized or the duration of exposure to high temperatures. In the extreme case, as much as 95% of the original cycloolefin monomer can be dissociated and the resulting products reacted with impurities and other cycloolefin monomers to form new species, generally of higher molecular weight. Dissociating and reacting about 5 to 50% by weight of the original cycloolefin monomer can be accomplished quite easily within a relatively short period of time at temperature values within the preferred range.

Where dicyclopentadiene is utilized as the only cycloolefin monomer, the cycloolefin products of a higher molecular weight predominantly include, in decreasing concentration, tricyclopentadiene, tetracyclopentadiene, pentacyclopentadiene, etc. Where dicyclopentadiene is the starting material and the heating period is less than 12 hours, resinous cycloolefin monomers with a degree of polymerization beyond pentacyclopentadiene are expected, but difficult to detect due to low concentrations.

Ethylidenenorbornene is an example of a comonomer for use in bulk polymerization reactions with dicyclopentadiene. Where it is added to the crude mixture of dicyclopentadiene, it will react with dissociated products to yield higher molecular weight cycloolefin monomers. Typical products from ethylidene norbornene include ethylidenetetracyclododecene, ethylidenehexacycloheptadecene, etc. Homologs of ethylidenenorbornene beyond ethylidenehexacycloheptadecene are difficult to detect because small quantities are present where the heating period is less than 12 hours. Vinylnorbornene, methylnorbornene are other common comonomers, and behave similarly.

A common alpha-olefin which may be added to the crude mixture of cycloolefin monomers is styrene, which will produce phenylnorbornene, phenyltetracyclododecene, phenylhexacycloheptadecene, etc. if reacted with cyclopentadiene during heat-soaking of dicyclopentadiene.

Polymerization grade mixtures of cycloolefin monomers are obtained from the process of the present invention. Such treated compositions provide a high degree of conversion when used as feedstocks in bulk polymerization reactions. Typical bulk polymerizations include reaction injection molding (RIM), reagent transfer molding (RTM) and liquid injection molding (LIM) techniques.

Also provided by this invention are methods for producing polymers obtained from ring-opening, bulk polymerization. These methods incorporate the heat treatment process of the present invention described above, wherein crude mixtures are heated to consume polymerization retarders. It is important that heating take place in the absence of the complete polymerization catalyst to prevent early polymer formation.

Subsequent to enhancing the polymerization activity of the crude mixture of cycloolefin monomers, a reactive liquid mixture is formed with the treated cycloolefin monomers. This reactive liquid mixture comprises a bulk polymerization catalyst/co-catalyst system and the treated cycloolefin monomers. This step can be performed simply by adding the complete catalyst system to the treated cycloolefin monomers or by adding any missing components i.e. either the catalyst or co-catalyst component, depending on which component was present in the crude mixture of cycloolefin monomers during heat-soaking. Suitable catalyst are the ammonium molybdates and tungstates previously described and suitable co-catalysts are the alkylaluminum halides described as suitable for bulk polymerization. When forming the reactive liquid mixture, the treated cycloolefins may be used as is or may be cooled or heated prior to forming the reactive liquid mixture.

Upon formation, the reactive liquid mixture is conveyed to a mold maintained at a temperature sufficiently high to initiate/accelerate ring-opening polymerization. Suitable mold temperatures fall in the range of 25° C. to 150° C.

By utilizing the bulk polymerization process of this invention, crude mixtures of one or more cycloolefin monomers can be used as starting materials. Using this invention, good monomer conversion can be obtained with a crude grade starting material. The polymers obtained therefrom are unique in that the less reactive linear olefins in this crude mixture are incorporated into the polymer chain and are not diluents or plasticizers. Suitable results are obtained utilizing crude mixtures of from 97% to 98% purity. Naturally, higher grades of purity are preferred and the process of this invention will provide beneficial results for crude mixtures of high monomer concentration, i.e. 98% to 99% but with significant amounts of polymerization retarder.

In performing some embodiments of the polymerization processes of the present invention, high molecular weight cycloolefin monomers are generated during heat-soaking, which are then polymerized. These processes incorporate heating conditions (duration, temperature, etc.) which render the crude mixtures of cycloolefin monomers an active polymerization grade feedstock and additionally provide cycloolefin monomers with increased molecular weight. For significant results, it is preferable that about 5% by weight of the cycloolefin monomers react with the cyclopentadiene product to provide high molecular weight species. Upon heating the crude mixture to obtain the desired polymerization activity or quality with an accompanying increase in monomer molecular weight, a reactive liquid mixture is formed as described above. This reactive liquid mixture comprises a bulk polymerization catalyst and the treated cycloolefin monomers with increased molecular weight. Upon formation, the reactive liquid mixture is conveyed to a mold maintained at a temperature sufficiently high to initiate ring-opening polymerization as described above.

Polymerization modifiers to control pot life may be used in the bulk polymerization reactions. Examples of such modifiers include water, methanol, ethanol, isopropyl alcohol, benzyl alcohol, phenol, methyl mercaptan, 2-chloroethanol, 1,3-dichloropropanol, p-bromophenol, epichlorohydrine, ethylene oxide cyclopentene-2-hydroperoxide, cumylhydroperoxide, tertiarybutyl peroxide, benzoyl peroxide, and air or oxygen. These are generally mixed with the alkylaluminum chloride component. Catalyst activators, which provide a source of halogen such as $SiCl_4$, may also be used to improve monomer conversion.

The polymer and copolymer products produced by the polymerization processes of this invention can include impact modifiers, antioxidants, flame retardants, pigments and the like. These products are generally in final form and any additives thereto must be introduced prior to polymerization.

The following examples are provided to better illustrate the invention. It should be recognized that this invention includes other embodiments which are not shown with the particularity of those below.

EXPERIMENTAL

General Procedure for Preparation of Bulk Polymerized Copolymers by a Simulated Reaction Injection Molding Process Two formulations of cycloolefin monomer are made, A and B. Formulation A is made by dissolving a trialkylammonium molybdate catalyst to a concentration of 0.1 normal in the cycloolefin monomer, preferably dicyclopentadiene. Formulation B is made by dissolving n-propanol catalyst modifier to 1 molar concentration, diethylaluminum chloride cocatalyst to 0.5 molar concentration and silicon tetrachloride catalyst activator to 0.25 molar concentration all within a second portion of cycloolefin monomer, preferably dicyclopentadiene. Samples of Formulation A and B are transferred to clean, dry bottles at room temperature and put under a nitrogen blanket. A pouring spout with a nitrogen inlet is put onto the formulation B bottle and the liquid contents injected into the formulation A bottle with shaking. The A/B bottle is fitted with a pouring spout and the contents transferred or injected into a cavity mold of about $\frac{1}{8}'' \times 8'' \times 8''$ held at about 70° C. A thermocouple inserted into the mold allows for monitoring of the temperature. Time to the reaction exotherm varies depending on numerous factors such as the mold temperature, amount of catalyst modifier and silicon tetrachloride catalyst activator, catalyst concentration. After the exotherm, usually about 1.5 to 3.0 minutes, the temperature drops down to the mold temperature (about 150° C.) and the mold is opened and the plaque removed.

Percent conversion is an important measurement and is done by thermalgravimetric analysis on the DuPont ® 1090 thermal analyzer using the weight loss on heating up to 400° C. as an indication of unreacted monomer. If a flame retardant is in the formulation, the weight loss just prior to the flame retardant decomposition is reported.

SMALL SCALE BULK POLYMERIZATION PROCESS

To speed up the process of preparing samples in the laboratory, the same results may be obtained as those from the procedure described under the heading "Experimental" by adding all the following ingredients sequentially: cycloolefin monomer or monomers, n-propanol catalyst modifier, cocatalyst, silicon tetrachloride catalyst activator and the trialkylammonium molybdate catalyst being added last. All these ingredients are added as part of a dicyclopentadiene solution.

EXAMPLES

The following examples demonstrate the enhancement of polymerization activity. Examples 1-3 and 7, 8 and 9, 10 show the polymerization of dicyclopentadiene treated by the process of this invention under different polymerization conditions. Controls of high purity (99%) dicyclopentadiene and a control of 97% dicyclopentadiene are provided to compare polymerization results of untreated samples. Examples 9, 10 show the use of feedstocks which contain elastomers.

EXAMPLES 1-3 AND CONTROL (EXAMPLE 4)

About 50 gal. of commercial crude grade 97% dicyclopentadiene obtained from Exxon, Inc. were heated to a temperature of about 150° C. for about 5 hours within a 50 gal. vessel under a $N_2$ blanket.

After cooling, 83 gms of dicyclopentadiene were prepared for bulk polymerization by the procedure described under the heading "Small Scale Bulk Polymerization Procedure" for each example. Three polymerizations were performed (Examples 1-3), with different n-propanol concentrations of 1.4, 1.8 and 2.2 millimols, respectively. These polymerizations were identified as 94-6-1, 94-6-2 and 94-6-3. It was discovered the reaction was too fast at the lower molar concentrations of n-propanol for manual transfer. Special equipment can be used to enhance the rate at which the materials are transferred. Polymer products of Examples 1 and 2 were not analyzed since proper transfer to the mold could not be accomplished.

In each of the examples, the quantity of diethylaluminum chloride co-catalyst was 2 millimoles, the quantity of silicon tetrachloride was 1 mol and the quantity of tridodecylammonium molybdate catalyst was 0.5 millimoles. All were introduced as a dicyclopentadiene solution. For Example 3, the reaction mixture was transferred to a mold maintained at about 70° C. The reactive sample achieved a maximum mold temperature of about 184° after 1 min. After cooling, the molded part was released and analyzed for percent conversion by thermal gravimetric analysis as described above under the heading "Experimental". The crude grade dicyclopentadiene, treated by the process of this invention, was found to attain about 97.6% conversion to polymer.

As a control (Example 4), another sample (about 83 gms) of commercial crude grade 97% dicyclopentadiene obtained from Exxon, Inc. was polymerized, without treatment by the process of this invention. This control, or Example 4, was identified as run 94-7. The same conditions as Example 1 were used except the reaction did not proceed as quickly so as to prevent transfer to the mold. The quantities of catalyst, cocatalysts, alcohol modifier and silicon tetrachloride were as reported for Example 1. The mold temperature was maintained at 70° C. and the thermocouple was found to read a maximum temperature of 120° C. after 1½ min. After the polymerized product was cooled and released from the mold, it was analyzed by a thermal gravimetric analysis as described above under the heading "Experimental". The untreated crude grade dicyclopentadine attained about 94.6% conversion to polymer product.

CONCLUSION

The process of the present invention provided an increase in polymerization activity of the crude grade dicyclopentadiene as shown by an increase in the degree of conversion from about 94.6% to about 97.6% and a decrease in reaction time from 1½ to one minute, even though more propanol modifier was used.

COMPARATIVE EXAMPLES 5-6

To establish a comparison of the treated crude grade dicyclopentadiene, two samples of commercial polymerization grade 99% dicyclopentadiene obtained from Exxon, Inc., identified as runs 48-5-1 and 48-5-2, were polymerized in accordance with the procedures described under the heading "Small Scale Bulk Polymerization Process." In each example, about 80 gms of 99% dicyclopentadiene were introduced into a dry bottle followed by 2 millimoles of n-propanol, 2 millimoles of diethylaluminum chloride co-catalyst, 1 millimole of silicon tetrachloride catalyst activator and 0.5 millimoles of tridodecylammonium molybdate as dicyclopentadiene solutions. The bottle was shaken and the contents transferred into a cavity mold of about ⅛"×8"×8" held at about 50° C. for each example. A thermocouple was mounted in the mold and the maximum temperature recorded for each example was about 162° C. during polymerization with reaction time to maximum temperature of 0.95 and 1 minute, respectively. After each polymerization was complete, the molded part was allowed to cool and it was then removed from the mold. Each molded part was analyzed for percent conversion as described in the disclosure under the heading "Experimental." The percent conversion was found to be 97.4% and 96.8% for each example, respectively.

EXAMPLES 7-8

About 400 gms of commercial crude grade 97% dicyclopentadiene obtained from Exxon, Inc. were heated to a temperature of about 165° C. for about 5 hours within a 1000 ml vessel under a $N_2$ blanket.

After cooling, 80 gms of the treated dicyclopentadiene were prepared for bulk polymerization for each of Examples 7 and 8 by the procedure described under the heading "Small Scale Bulk Polymerization Process." Examples 7 and 8 polymerization runs were identified as 94-5-1 and 94-5-2, respectively. Each polymerization run utilized different quantities of n-propanol catalyst modifier. In Example 7, 1.8 millimoles of n-propanol were used while in Example 8, 1.4 millimoles of n-propanol were used. For each of Examples 7 and 8, The quantity of diethylaluminum chloride co-catalyst was 2 millimoles, the quantity of silicon tetrachloride activator was 1 millimole and the quantity of tridodecyl ammonium molybdate was 0.5 millimoles.

Each of Examples 7 and 8 were molded in accordance with the procedures defined under the heading "Experimental." The mold temperature for Example 7 was about 60° C. and the reagents achieved a maximum temperature of 155° C. in 3 min. For Example 8, the mold temperature was 70° C. and the reagents achieved a maximum temperature of 170° C. in 0.8 min. The longer reaction time in Example 7 relates to the higher alcohol level. After reaction was complete, the molded part was allowed to cool and then removed from the mold. The degree of conversion was determined by thermal gravimetric analysis on a duPont 1090 thermal analyzer for each of Examples 7 and 8. Weight loss at 400° C. was taken as an indication of unreacted monomer. For Example 7, the percent conversion was 95.5%. For Example 8, the percent conversion was 97.2%.

COMPARATIVE EXAMPLES

To provide a general comparison, two polymerizations were run which were identified as runs 212-1 and 212-2. In each of these runs, samples of the crude grade 97% dicyclopentadiene described in Examples 7 and 8, were polymerized without treatment. The monomers were mixed with similar quantities of catalyst, co-catalyst, and $SiCl_4$ activator. For run 212-1, 1.5 millimoles of propanol were added. For run 212-2, 1.3 millimoles of propanol were added. The mold temperatures were maintained at 55° C. (Reaction 212-1 peaked at 94° C. after 4 min., 212-2 at 76° C. in 5 min. 15 sec.) The degree of conversion for run 212-1 was 94.1% and for run 212-2, it was 91.5%.

CONCLUSION

These examples show an improvement in polymerization activity for 97% pure dicyclopentadiene when treated by the process of this invention.

EXAMPLES 9 and 10

Two additional samples of the treated crude grade 97% dicyclopentadiene, reported in Examples 7 and 8 were used for Examples 9 and 10.

About 81 gms dicyclopentadiene were prepared for bulk polymerization by the procedure described above under the heading "Small Scale Bulk Polymerization Procedure" for each example. These examples were identified as runs 98-5 and 98-6. For both Examples, the following were added to the dicyclopentadiene: 4 ml of 0.5 molar diethylaluminum chloride co-catalyst, 2.2 ml of 1.0n molar n-propanol, and 5 ml of 0.1N tridodecylammonium molybdate and 4 ml of 0.25 molar silicon tetrachloride all in dicyclopentadiene solutions. For Example 9, 1.5 gms of elastomer Vistanex MML-80 were added. For Example 10, 2.5 gms of Diene 55 elastomer were added. These ingredients were combined, shaken and injected into a mold cavity having the dimensions $\frac{1}{8} \times 8'' \times 8''$. The mold temperature was maintained at 50° C. for Example 9 and 60° C. for Example 10. The maximum temperature achieved during polymerization in Example 9 was about 132° C. in 2.6 min. while the maximum temperature in Example 10 was about 149° C. in 2.2 min. After the reaction was complete, the molded part was allowed to cool and was then removed from the mold. The percent conversion was determined utilizing thermal gravimetric analysis with a DuPont 1090 thermal analyzer using the weight loss on heating up to 400° C. as an indication of unreacted monomer. The percent monomer conversion for Example 9 was 96.6% and the percent conversion for Example 10 was 97.3%.

CONCLUSION

These examples show the treatment of crude grade dicyclopentadiene by the process of this invention provides high monomer conversions even where additives, such as elastomers are present.

While the invention has been disclosed in this patent application by reference to the details of preferred embodiments of the invention, it is to be understood that this disclosure is intended in an illustrative rather than in a limiting sense, as it is contemplated that modifications will readily occur to those skilled in the art, within the spirit of the invention and the scope of the appended claims.

What is claimed is:

1. A method for enhancing the polymerization activity of crude grade cycloolefin monomers comprising:
   providing a crude grade monomer mixture of one or more cycloolefin monomers having at least one norbornene functional group, said crude grade mixture containing polymerization retarding impurities in amounts sufficient to reduce the degree of monomer conversion upon polymerization by at least 1%, as measured by thermal gravimetric analysis on a thermal analyzer utilizing the weight loss of a polymerized sample up to 400° C. as the weight of unreacted monomer;
   said crude grade monomer mixture containing at least about 10 weight percent dicyclopentadiene monomer, based on the total weight of the crude grade mixture;
   heating said crude grade monomer mixture to a temperature sufficiently high and for a period sufficiently long to dissociate a portion of the dicyclopentadiene monomers to cyclopentadiene and to react said cyclopentadiene with the polymerization retarding impurities in a quantity sufficient to increase the degree of monomer conversion by at least 1% as measured by thermal gravimetric analysis on a thermal analyzer utilizing the weight loss of a polymerized sample up to 400° C. as the weight of unreacted monomer;
   wherein the crude grade monomer mixture is maintained free of a complete polymerization catalyst/co-catalyst system.

2. A method as in claim 1 wherein the polymerization retarding impurities in said crude grade monomer mixture comprise linear olefinic impurities.

3. A method as in claim 1 wherein the polymerization retarding impurities in said crude grade monomer mixture comprise linear olefinic impurities in an amount of from about 0.25 weight percent up to about 10 weight percent of the crude grade monomer mixture.

4. A method for enhancing the polymerization activity of crude grade cycloolefin monomers comprising:
   providing a crude grade monomer mixture of one or more cycloolefin monomers having at least one norbornene functional group, said crude grade monomer mixture containing polymerization retarding impurities comprising linear olefinic impurities in an amount of from 1% to 10% by weight based on the weight of the total crude grade monomer mixture;
   said crude grade monomer mixture containing at least about 25 weight percent dicyclopentadiene monomer, based on the total weight of the total crude grade monomer mixture;
   heating said crude grade monomer mixture to a temperature sufficiently high and for a period sufficiently long to dissociate a portion of the dicyclopentadiene monomers to cyclopentadiene and reacting the cyclopentadiene with the linear cycloolefinic impurities in an amount sufficient to provide an increase in the degree of monomer conversion of at least 1%, as measured by thermal gravimetric analysis on a thermal analyzer utilizing the weight loss of a polymerized sample up to 400° C. as the weight of unreacted monomer;
   wherein the crude grade monomer mixture is maintained substantially free of a complete polymerization catalyst/co-catalyst system.

5. A method as in claim 4 wherein the one or more cycloolefin monomers are comprised substantially of dicyclopentadiene.

6. A method as in claim 4 wherein the crude grade monomer mixture of one or more cycloolefin monomers additionally comprises one component selected from the group consisting of catalysts for ring-opening polymerization in bulk and co-catalysts for ring-opening polymerization in bulk.

7. A method as in claim 4 wherein the crude grade monomer mixture of one or more cycloolefin monomers is heated to a temperature in the range of about 60° C. to about 250° C. for a period of at least about 0.25 hours.

8. A method for enhancing the polymerization activity of crude grade cycloolefin monomers comprising:
   providing a crude grade monomer mixture of one or more cycloolefin monomers having at least one norbornene functional group, said crude grade mixture comprising from 1 to 10% by weight linear olefinic impurities and oxygen containing impurities, said crude grade monomer-mixture containing at least about 25 weight percent dicyclopentadiene monomer, based on the total weight of the mixture;
   heating the crude grade monomer mixture to a temperature in the range of about 100° C. to about 175° C. for a period of from 1 to 6 hours;
   wherein the crude grade monomer mixture is maintained substantially free of a complete polymerization catalyst/co-catalyst system.

9. A composition produced by the process of claim 8.

10. A composition as in claim 9 obtained from commercial crude grade 97%–98% dicyclopentadiene which exhibits a degree of monomer conversion upon polymerization that is equal to or greater than commercial polymerization grade 99% dicyclopentadiene.

11. A method for producing ring-opened polymerized polymers comprising:
   (a) providing a crude grade monomer mixture of one or more cycloolefins having at least one norbornene functional group, said crude grade monomer mixture comprising about 1 to 10% by weight linear olefinic impurities and at least about 25% by weight dicyclopentadiene;
   (b) heating the crude grade monomer mixture to a temperature sufficiently high and for a period sufficiently long to dissociate a portion of the dicyclopentadiene monomer to cyclopentadiene and to react the cyclopentadiene with the linear olefinic impurities in an amount sufficient to increase the degree of monomer conversion by at least 1% as measured by thermal gravimetric analysis on a thermal analyzer, utilizing the weight loss of a polymerized sample up to 400° C. as the weight of unreacted monomer;
   wherein the crude grade monomer mixture is maintained substantially free of a complete ring-opening polymerization catalyst/co-catalyst system during step (b);
   (c) forming a reactive liquid mixture comprising the heated crude grade monomer mixture of step (b) and a complete ring-opening bulk polymerization catalyst/co-catalyst system; and
   (d) conveying said reactive liquid mixture into a mold maintained at a temperature sufficiently high to thermally accelerate ring-opening polymerization.

12. A method as in claim 11 wherein the crude grade monomer mixture is heated to a temperature in the range of about 60° C. to about 250° C. for a period of at least about 0.25 hours in step (b) and the crude grade monomer mixture comprises commercial crude grade 97%–98% dicyclopentadiene.

13. A method for producing high molecular weight ring-opening polymerized polymers comprising:
   (a) providing a commercial crude grade 97%–98% dicyclopentadiene monomer which comprises polymerization retarding impurities in an amount sufficient to provide a degree of conversion below 95% as measured by thermal gravimetric analysis on a DuPont 1090 thermal analyzer utilizing the weight loss of a polymerized sample up to 400° C. as the weight of unreacted monomer.
   (b) heating the crude grade dicyclopentadiene to a temperature in the range of about 140° C. to about 175° C. for a period of about 1 to 6 hours to dissociate a portion of the dicyclopentadiene monomers to cyclopentadiene and react the cyclopentadiene with both dicyclopentadiene and the polymerization retarding impurities in an amount sufficient to increase the degree on monomer conversion by at least 1% as measured by thermal gravimetric analysis on a DuPont 1090 thermal analyzer utilizing the weight loss of a polymerized sample up to 400° C. as the weight of unreacted monomer;
   wherein the crude grade dicyclopentadiene is maintained substantially free of a complete bulk polymerization catalyst/co-catalyst system during step (b);
   (c) forming a reactive liquid mixture comprising the heated crude grade dicyclopentadiene and a complete ring-opening, bulk polymerization catalyst/co-catalyst system and
   (d) injecting said reactive liquid mixture into a mold maintained at a temperature sufficiently high to thermally accelerate ring-opening polymerization.

14. A method as in claim 13 wherein heating the commercial crude grade 97%–98% dicyclopentadiene provides a cycloolefin monomer mixture having a degree of monomer conversion of greater than about 97%.

15. A composition comprising a polymer produced in accordance with the method of claim 13.

16. A composition as in claim 15 additionally comprising additives selected from the group consisting of flame retardants, anti-oxidants, impact modifiers and pigments.

* * * * *